United States Patent [19]
Szelke et al.

[11] Patent Number: 4,650,661
[45] Date of Patent: Mar. 17, 1987

[54] ENZYME INHIBITORS

[75] Inventors: Michael Szelke, Ruislip; David M. Jones, Hayes; Allan Hallett, Cheam, all of England

[73] Assignee: Aktiebolaget Hassle

[21] Appl. No.: 462,928

[22] Filed: Feb. 1, 1983

[30] Foreign Application Priority Data

Sep. 15, 1982 [GB] United Kingdom ............... 8226273

[51] Int. Cl.$^4$ ................. A61K 49/00; A61K 37/43; C07K 5/02; C07K 7/06
[52] U.S. Cl. ........................................ 424/9; 514/16; 514/17; 530/323; 530/328; 530/329
[58] Field of Search ............ 260/112.5 R; 424/9; 514/16, 17; 530/323, 328, 329

[56] References Cited

U.S. PATENT DOCUMENTS

| | | | |
|---|---|---|---|
| 4,198,398 | 4/1980 | Hudson et al. | 260/112.5 R |
| 4,424,207 | 1/1984 | Szelke et al. | 260/112.5 R |
| 4,470,971 | 9/1984 | Boger et al. | 260/112.5 R |

FOREIGN PATENT DOCUMENTS

| | | |
|---|---|---|
| 0045665 | 2/1982 | European Pat. Off. . |
| 0077028 | 4/1983 | European Pat. Off. . |
| 0077029 | 4/1983 | European Pat. Off. . |
| 0081783 | 6/1983 | European Pat. Off. . |
| 0081094 | 6/1983 | European Pat. Off. . |
| 2003481 | 3/1979 | United Kingdom . |

OTHER PUBLICATIONS

Parsons, *Peptide Hormones*, University Park Press, Baltimore, pp. 1-7.
Ariens, *Drug Design*, II, Academic Press, Inc. N.Y. 1971, Chapter 9, p. 337.
Blundell et al., *Nature*, vol. 304, 1983, pp. 273-275.
Nishizawa et al., *Journal of Medicinal Chemistry*, vol. 20, No. 4, 1977, pp. 510-515.
Rich et al., *Biochemical and Biophysical Research Communications*, vol. 74, No. 2, 1977, pp. 762-767.
Rich et al., *J. Org. Chem.*, vol. 43, No. 18, 1978, pp. 3624-3626.

*Primary Examiner*—Delbert R. Phillips
*Attorney, Agent, or Firm*—Larson and Taylor

[57] ABSTRACT

Renin inhibitory polypeptide analogues derived from the natural N-terminal substrate sequence by replacing the amino acid at position 10 with statine or a residue related to it.

55 Claims, No Drawings

ENZYME INHIBITORS

The invention relates to renin-inhibiting peptide analogues.

BACKGROUND

Renin is a natural enzyme, disorders in relation to which are implicated in many cases of hypertension. It is released into the blood from the kidney, and cleaves from a blood glycoprotein a decapeptide known as angiotensin-I. Circulating angiotensin-I is cleaved in lung, kidney and other tissues to an octapeptide, angiotensin-II, which raises blood pressure both directly by causing arteriolar constriction and indirectly by stimulating release of the sodium-retaining hormone aldosterone from the adrenal gland and thus causing a rise in extracellular fluid volume. The latter effect is caused by angiotensin-II itself or a heptapeptide cleavage product angiotensin-III.

Inhibitors of renin have therefore been sought, with two ends in view, first the provision of a diagnostic agent for identification of cases of hypertension due to renin excess, and secondly the provision of an agent for control of hypertension in such cases.

The present inventors' approach has been to consider the peptide sequence characterising the natural renin substrate at its binding site, and to seek peptide analogues sufficiently similar to bind to the enzyme, in competition with the natural substrate, but sufficiently dissimilar to it to be cleaved slowly or not at all. Such analogues will block the action of the enzyme and attack the hypertension at source.

Renin is specific to a particular bond in the substrate, the N-terminal sequence of which in the horse is for example:

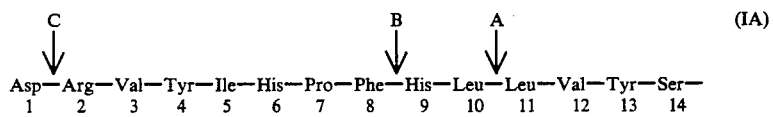

(IA)

as found by L. T. Skeggs et al J. Exper. Med. 106 439 (1957). Human renin substrate has a different sequence recently discovered by D. A. Tewkesbury et al Biochem. Biophys. Res. Comm. 99 1311 (1981)

(IB)

the sequence to the left of the arrow A being as in formula (IA).

Cleavage at A gives angiotensin-I; subsequent cleavage at the Phe-His bond at B gives angiotensin-II; and cleavage subsequently again at the Asp—Arg bond at C gives angiotensin-III.

Peptides similar to certain partial sequences of the substrate have been shown to act as inhibitors of renin in vitro. An example is the tetrapeptide ester (the relation to the substrate residues being indicated by numbering):

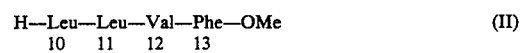

(II)

proposed by Kokubu, Nature, 217 456 (1968(but it is inactive in vivo, because of binding to plasma proteins and rapid attack by natural peptidases.

One of the present inventors undertook some years ago a development of Kokubu's work, seeking a renin inhibitor active, in vivo, in which analogues of peptides similar to Kokubu's were made but having a methylene imino group —CH$_2$—NH— in place of the peptide link —CO—NH— between the leucine residues. One of these analogues was:

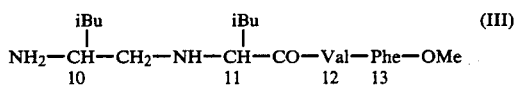

which is the tetrapeptide (I) modified at the Leu—Leu link, leucine of course being

This analogue (III) was the first effective in-vivo inhibitor of renin and was shown to have significant antihypertensive action in Goldblatt hypertensive rats (Parry, Russell and Szelke p. 541 in "Chemistry and Biology of Peptides" Ed. Meienhofer, Ann Arbor Science Publishers 1972). Little or no attention has however been paid to the work, which the authors themselves were unable to pursue, in spite of considerable activity in the general field of substrate-based inhibitors for renin, reviewed for example by Haber & Burton, Federation Proc. 38 No. 13 2768-2773 (1979).

THE INVENTION

The present invention is a development of the above work, to which the inventors were stimulated by consideration of the acid protease inhibitor pepstatin further considered later herein. It contains the acid statine NH$_2$CH(iBu)CH(OH)CH$_2$COOH, an amino acid (though not an alpha amino acid as the common natural amino acids are) and appeared to the inventors to offer scope for work related to though on different lines from their work on peptide analogues disclosed for example in their U.S. patent application Ser. No. 290 620 filed Aug. 5, 1981 (published as European Patent Specification No. 0 045 665 on Feb. 10, 1982).

In those analogues a peptide bond is represented by other links corresponding to partial or complete reduction at the carbonyl group and/or replacement of the nitrogen (—NH—) group by a methylene group. The inventors have however now surprisingly found that notional replacement of the carbonyl group by a number of 2-, 3- or 4-carbon groups including but by no means restricted to the group seen in statine gives renin-inhibiting peptide analogues of high specificity and activity. This is so even though the structural relation to the polypeptide that is the natural substrate of renin is less than previously. Low activity would be expected and, further, loss of specificity as for example with pepstatin itself.

Thus behind both inventions is a concept of modified peptide structures related to the peptide sequence at the site of action of renin on the natural substrate, by substitution at the site of cleavage, but the two approaches are distinct.

Optionally further in the present invention there is isosteric substitution, or other modification, at other positions to increase stability or to modify the properties of the final peptide, for example its solubility under physiological conditions or its resistance to degradation in vivo. Such modification may for example be by incorporation of residues other than those of the natural L-amino acids; by protection of the N-terminus with acetyl, pivaloyl, t-butyloxycarbonyl (Boc), benzoyl or other groups; or by conversion of the C-terminal carboxyl to another functional group, e.g. the corresponding alcohol, present as such or in ether or ester form.

THE PRESENT COMPOUNDS DEFINED

General reference to amino acids and amino acyl residues and side chains in both the description and claims herein is to be taken as reference to such whether naturally occurring in proteins or not and to both D- and L-forms, and amino is to be taken as including imino.

The compounds of the present invention, showing desirable renin inhibitory action, are of the general formula:

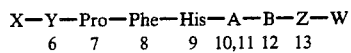

6   7    8     9  10,11 12  13 or the partial sequences:

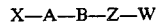     (V) (i)

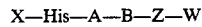     (V) (ii)

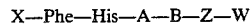     (V) (iii)

     (V) (iv)

where:
Pro, Phe, and His may be in substituted form, e.g. carrying OH, F, Cl, Br or Me;

X=H; or an acyl or other N-protecting group e.g. acetyl, pivaloyl, benzyloxycarbonyl, t-butyloxycarbonyl (Boc), benzoyl or lower alkyl (primarily $C_1$–$C_5$); or an D- or L-amino acyl residue (especially Pro), which may itself be N-protected similarly:

Y=D- or L-His or other D- or L-basic or aromatic amino-acyl residue, or is absent;

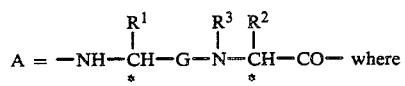

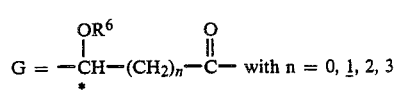

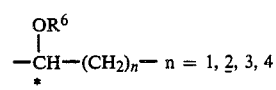

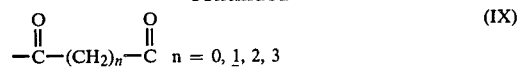

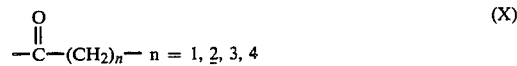

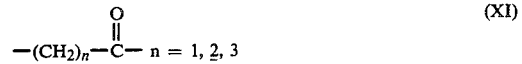

and where the configuration at asymmetric centres * is either R or S, $R^1$ and $R^2$, the same or different, being=$^i$Pr (isopropyl), $^i$Bu (isobutyl), Bzl (benzyl) or other amino-acid side chain preferably lipophilic or aromatic;

$R^3$=H; lower alkyl ($C_1$–$C_5$); or t-butyloxycarbonyl, benzyloxycarbonyl, ring substituted benzyloxycarbonyl, —$SO_2PH$, —$SO_2C_6H_4CH_3(p)$, formyl or other N-protecting group including lower acyl ($C_1$–$C_5$) generally;

$R^6$=H, or lower alkyl, lower acyl, benzyl, tetrahydropyranyl, or other hydroxyl protecting group;

B=D- or L-Val Leu or Ile or other D- or L-lipophilic amino-acyl residue;

Z=D- or L-TYr, Phe, His or other L- or D-aromatic amino-acyl residue; and

W=(i) —OH as such or in protected ester form e.g. as —$OR^4$ where $R^4$=lower alkyl primarily $C_1$–$C_5$ and particularly $^t$Bu, or cycloalkyl primarily $C_3$–$C_7$, or Bzl, or other ester forming group; or (ii) —$NH_2$, as such, or in protected amide form as —$NHR^5$ or —$N(R^5)_2$ (where $R^5$=an N-protecting or other substituent group e.g. lower alkyl as for $R^4$ and $(R^5)_2$=two such groups or e.g. cyclo-alkyl, primarily $C_3$–$C_7$), or as —NH—$(CH_2)_n$—Q or —$NR^5$—$(CH_2)_n$—Q (where n=2 to 6 and Q=$NH_2$ or

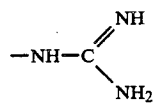

and wherein any of the hydrogens attached to nitrogen may be substituted by $R^5$ or $(R^5)_2$; or (iii) an D- or L-serine or D- or L-lysine, arginine or other basic amino-acyl residue as such or in amide form, substituted amide form or ester form e.g. containing a group or groups as given for $R^4$ and $R^5$ above as the case may be; or (iv) an amino alcohol residue derived therefrom as such or protected in ester or ether form e.g. containing a group as given for $R^4$ above or Z+W=an alcohol derived from L- or D-Tyr, Phe or His or other L- or D-aromatic amino-acyl residue as such or protected in ester or either form as above;

such polypeptide being in the above form or modified by isosteric replacement of one or more remaining peptide bonds, for example by reduced —$CH_2$—NH—, keto,

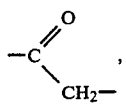

hydroxy, —CH(OH)—CH₂—, or hydrocarbon —CH₂—CH₂— isosteric links in the form:

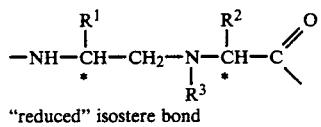

"reduced" isostere bond or

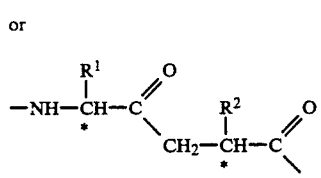

"keto" isostere bond or

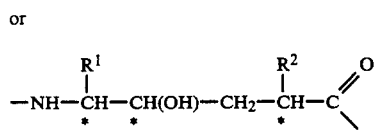

"hydroxy" isostere bond or

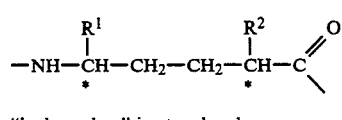

"hydrocarbon" isostere bond where the significance of *, $R^1$, $R^2$ and $R^3$ is as before; and said polypeptide further being in free form or in protected form at one or more remaining amino or amide (including peptide) nitrogen, carboxyl, hydroxy or other reactive groups, or in salt form at amino, imidazole or carboxyl groups, in particular as their physiologically acceptable acid addition salts at basic centres.

The above compounds may in particular be those related to the substrate sequence in the horse (B=Val at position 12) or those related to the substrate sequence in man (B=Ile at position 12). Particular groups of these compounds are set out in the formulae below, either:

(A) X—Y—Pro—Phe—His—A—Val—Z—W     (VA)
    6  7   8     9 10,11 12 13 where
X, Y, Pro, Phe and His are as before A is as before except that
$R^1$ and $R^2$, the same or different=$^i$Bu (isobutyl), $^i$Pr or Bzl (benzyl) or other amino-acid side chain preferably lipophilic or aromatic
$R^3$=H; or —SO₂Ph, —SO₂C₆H₄CH₃(p), Boc, formyl or other N-protecting group
$R^6$=lower alkyl, lower acyl, benzyl, tetrahydropyranyl, or other hydroxyl protecting group
Z=Tyr, Phe or other L- or D-aromatic amino-acyl residue;
W=—OH as such or in protected ester form as —OR⁴ where R⁴=lower alkyl (primarily C₁-C₅ and particularly $^t$Bu), or Bzl, or other ester forming group; or —NH₂ as such or in protected amide form as —NHR⁵ or —N(R⁵)₂ (R⁵=an N-protecting group e.g. lower alkyl as for R⁴; (R⁵)₂=two such or e.g. cyclo-alkyl, primarily C₃-C₇) or an L- or D-amino-acyl residue e.g. a serine or basic amino-acyl residue as such or in amide form or in protected amide or ester form e.g. containing a group or groups as given for R⁴ and R⁵ above as the case may be; or an amino acid alcohol residue derived therefrom as such or protected in ester or ether form e.g. containing a group as given for R⁴ above or Z+W=an alcohol derived from Tyr or Phe or other L- or D-aromatic amino acyl residue as such or protected in ester or ether form as above; or:

(B) X—Y—Pro—Phe—His—A—Ile—Z—W     (VB)
    6  7   8     9 10,11 12 13 where
X, Y, Pro, Phe and His are as before
A is as before except that
$R^1$=$^i$Bu (isobutyl) or Bzl (benzyl) or other amino-acid side chain preferably lipophilic or aromatic
$R^2$=$^i$Pr (isopropyl), and
$R^3$=H; or —SO₂Ph, —SO₂C₆H₄CH₃(p), Boc, formyl or other N-protecting group
$R^6$=lower alkyl, lower acyl, benzyl, tetrahydropyranyl, or other hydroxyl protecting group
Z is as before
W is as in formula (VA) or Z+W=an alcohol derived from the aromatic residues specified for Z before, as such or protected in ester or ether form as specified therein.

The numbering of residues in formula (V), (VA) and (VB) shows the correspondence with the renin substrates themselves, but without limitation of the generality of the formulae.

Substitutes for Pro Phe and His above may for example be: (1) for Pro 4-hydroxyproline (HPro) or pGlu (2) for Phe: Tyr, Phe(4—Cl), Phe(4—F) (3) for His: His(Me), Spinacin.

Reference to basic and aromatic amino acids above, and to amino acids with lipophilic side chains includes but is not restricted to the common amino acids of those classes, viz:

| | | |
|---|---|---|
| Basic: | Arginine | |
| | Lysine | |
| | Histidine | |
| Aromatic: | Phenylalanine | |
| | Tyrosine | |
| | Tryptophan | |
| | Histidine | |
| Lipophilic: | Leucine | Phenylalanine |
| | Isoleucine | Cyclohexylalanine ⎫ unnatural |
| | Valine | Adamantylalanine ⎭ |

Suitable amino acyl residues X may for example be those of: D or L Pro, Val or Ile; Gly.

Where a peptide bond in addition to that corresponding to the Leu—Leu or Leu—Val bond in the natural renin substrate is modified, the 7,8 and 8,9 positions i.e. the Pro—Phe and Phe—His bonds in formula V are preferred, or possibly both of these positions, and it is further preferred that the substitution should be

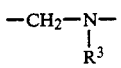 (XVII)

i.e. as a "reduced" isostere bond XIII, where R³ is as set out above. The alternative isosteric substitutions set out herein may however be used.

Protective or substituent groupings as mentioned above may be any of these known in the polypeptide art, amply disclosed in the literature and not requiring discussion at length here. Generally the selection of the groups is according to their function, some being primarily intended to protect against undesired reaction during synthetic procedures while the N- and C-terminal substituents are for example directed against the attack of enzymes on the final compounds or to increase their solubility and hence physiological acceptability. All these functions are generally within the terms "protective group" or the like used herein, including the claims. It is in particular possible for one or more remaining peptide bonds in the compounds of formula (V), (VA) or (VB) to be N-substituted.

STATINE

A particular representative of the group

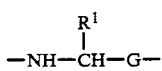 (XVIII)

above is the S,S-statine residue (Sta)

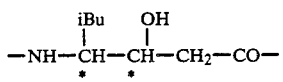 (XIX)

Statine itself is a known compound occurring in nature in the protease inhibitor pepstatin isolated in 1970 by Japanese workers from various Actinomycetes (Morishima et al J. Antibiot. 13 No. 5 259-265 (1970)) of formula:

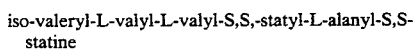 (XX)

or, in the usual notation:

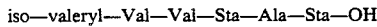 (XXI)

It inhibits acid proteases in general, so called because the catalytic functional groups are carboxyl groups of aspartic acid residues (as opposed to serine residues in serine proteases). Pepsin, cathepsin D, chymosin and renin are some of the representatives of this class of enzymes, and all are inhibited by pepstatin.

Incorporated however for example in the compound

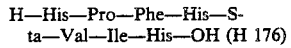 (XXII)

statine when tested by the methods in our published European specification gives IC$_{50}$=0.016 μM against human renin. This compound is the subject of Example 1 below.

APPLICATIONS

The invention further lies (i) In a diagnostic test for high renin states, blood pressure falling most when renin is high, and a surgical prognostic test for reno-vascular hypertension (renal artery stenosis), by the administration of a polypeptide analogue as above followed by monitoring of blood pressure, and such polypeptide analogues when for such use, and (ii) In the long and short term treatment of heart failure and all forms of hypertension particularly those associated with high serum renin levels, by the administration of a renin-inhibiting amount of a polypeptide analogue as above, and such polypeptide analogues when for such use.

The long and short term response of blood pressure to renin inhibitors is predictive of surgical outcome. In all cases single and repeated doses and any conventional form of pharmaceutical composition may be used, for administration by intranasal or oral route, injection, or any other means as convenient. Amounts may for example be 0.001 to 10 mg/kg body weight daily more usually 0.01 to 1 mg, according to the potency of the analogue and the severity of the condition. Dosage unit compositions may contain such amounts or submultiples thereof to make up the daily dose. (Dosages herein are related to the free base content where compounds are in salt form.)

SYNTHETIC METHODS

The inventors have developed synthetic methods for the isosteric replacement of the peptide bond —CON— with alternative groups, specifically —CH$_2$—NH— (reduced), —CH$_2$CH$_2$ (hydrocarbon),

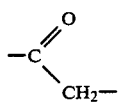

(keto) and —CH(OH)—CH$_2$— (hydroxy) isosteres as referred to earlier herein, see e.g. Szelke, et al, pp. 57-70 in "Molecular Endocrinology" Vol. 1, Editors: MacIntyre and Szelke, Elsevier, Amsterdam 1977; Hudson, Sharpe and Szelke, U.S. Pat. No. 4,198,398 "Enkephalin Analogues"; and Szelke, Jones and Hallett (Ferring Pharmaceuticals Ltd. and Ferring AB) in the published European specification already referred to.

Reference may be made to these publications for general discussion of such isosteric replacement and, in the European specification, for discussion in relation to renin inhibitors particularly. Reaction sequences for the preparation of peptide analogues applicable in the context of the present invention, apart from the link at A, are given there.

Turning therefore to the link at A, first there are several known syntheses of statine (XXIII below) available, e.g. that by D. H. Rich et al, J. Org. Chem. 1978, 43, p. 3624 and references quoted therein. Deoxystatine (XXIV below) has also been described (D. H. Rich et al, BBRC 1977, 74, p. 762), as has the synthesis of norstatine (XXV below) and its various analogues (R. Nishizawa et al, J. Med. Chem. 1977, 20, p. 510).

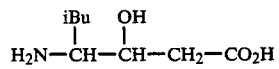 (XXIII)

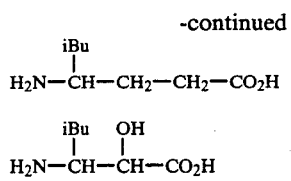  (XXIV)

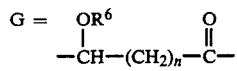  (XXV)

Of these, comparing with the possibilities for G given earlier, XXIII has

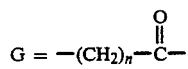

where $R^6 = H$ and $n = 1$; XXIV has

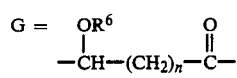

where $n = 2$; and XXV has

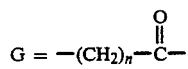

wherein $R^6 = H$ and $n = 0$.

For example, the following specific compounds have been made:

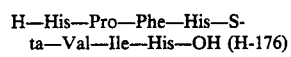  (XXII)

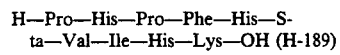  (XXXVI)

Their preparation was carried out by the procedures generally as described in our published European specification, and given in detail in the Examples which appear below. Statine was incorporated in the form of Nα-Boc-statine, using DCCI and HOBt as coupling reagents.

Other structures for G of particular value are:

1  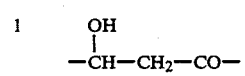  (XXVI)

2  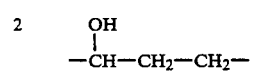  (XXVII)

3    (XXVIII)

4  —CH₂—CH₂—CO—  (XXIX)

5  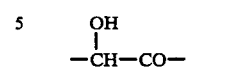  (XXX)

6  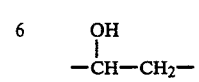  (XXXI)

7    (XXXII)

8  —CH₂—CO—  (XXXIII)

9  $\underset{\parallel}{-\text{C}}-\text{CH}_2-$  (XXXIV)

Syntheses of these, generally applicable but given by way of example in the context of the detailed synthesis of Example 1 and thus giving octapeptide analogues of H-176 containing the various structures, are respectively as follows, referring to the reaction schemes given below:

1—By coupling of Boc—Sta—OH to the appropriate protected peptide, which in the synthesis for example of H-176 is H—Val—Ile—His(Bom)—O R (LVI) ( R =resin support)

2—By coupling compound L (Scheme II below, R=H) to H—Ile—His—(Bom)—O R (LVII)

3—By oxidising Boc—statine with pyridinium dichromate and coupling the resultant keto acid Boc—NH—CHR¹—CO—CH₂—CO₂H  (XXXVII)

($R^1 = {}^i$Bu) to the tripeptide ester LVI above

4—By coupling Boc-deoxy-statine

Boc—NH—CHR¹—CH₂—CH₂—CO₂H  (XXXVIII)

($R^1 = {}^i$Bu) prepared according to Rich et al, BBRC 1977, 74, p. 762, to the tripeptide ester LVI.

5—By coupling Boc—nor—statine (obtained according to R. Nishizawa et al, J. Med. Chem. 1977, 20, p. 510) to the tripeptide ester LVI.

6—By coupling compound XLVI (Scheme I below, R=H) to the dipeptide ester LVII above.

7—By oxidising Boc—nor—statine to the corresponding keto acid

Boc—NR—CHR¹—CO—CO₂—H  (XXXIX)

and coupling the latter to the tripeptide ester LVI.

8—By coupling Boc—NH—CHR¹—CH₂—CO₂H obtained by one cycle of the Arndt-Eistert reaction from Boc—NH—CHR¹—Co₂H,) to the tripeptide ester LVI.

9—By oxidising the hydroxyl group in compound XLVI (Scheme I, R=H) to a keto group and coupling the resultant dipeptide analogue to the dipeptide ester LVII.

The same methods are applicable in making compounds corresponding to that of Example 2.

Scheme I

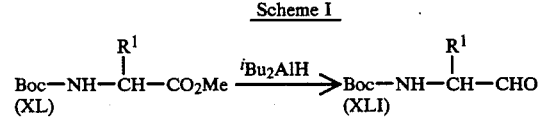

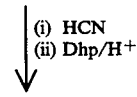

-continued
Scheme I

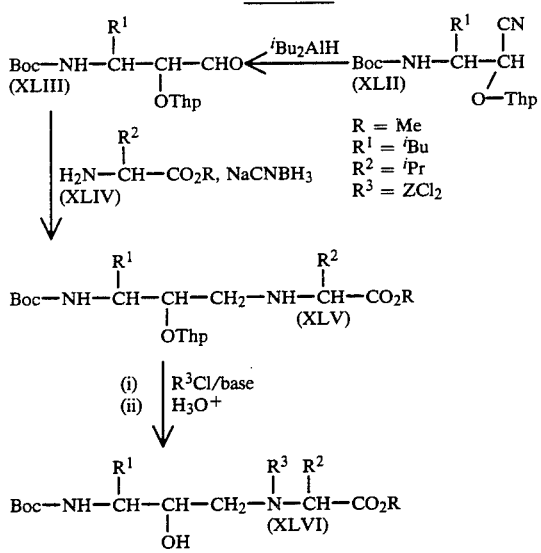

Scheme II

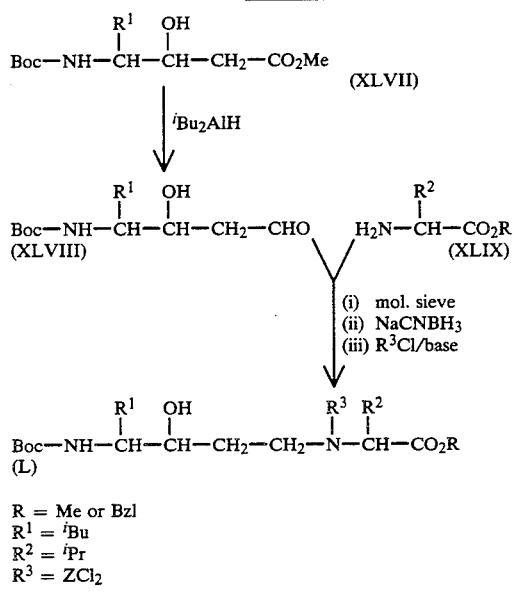

R = Me or Bzl
R¹ = ⁱBu
R² = ⁱPr
R³ = ZCl₂

EXAMPLES

The following are the fully detailed examples referred to earlier. The activity of H-176 (Example I) has already been given. Preliminary results for H-189 (Example II) indicate still higher activity, IC$_{50}$ 0.009 μM against human renin and 0.012 μM against baboon renin.

EXAMPLE 1

H-176
H—His—Pro—Phe—His—S-
ta—Val—Ile—His—OH       (XXII)

Boc-His(π—Bom)—O—Resin (1 g, 0.2 mmol) was washed with reagents as described in European Application No. 0 045 665 Example I. Subsequent deprotections and coupling reactions were carried out by using the same sequence of washes and reaction times with the following modifications.

During the coupling of Boc—Sta—OH to H—Val—Ile—His—(π—Bom)—O—Resin, the reaction was allowed to proceed for 16 hrs and 0.27 mmoles of Boc—statine were used. For all the other coupling reactions, 0.8 mmoles of Boc—amino acids were used.

After the final coupling, followed by acetylation for 1 hr, the resin was washed and dried to give 0.926 g of product.

This material was treated with HF at 0° for 1¼ hrs. in the presence of anisole (1 ml) and dried overnight over potassium hydroxide. The resin was washed with acetic acid/water (1:1) (100 ml) to remove the peptide. Evaporation of volatiles afforded a residue which upon drying over KOH under high vacuum weighed 126 mgs.

This material was applied to a Sephadex G.25 column (82×2.5 cm), eluted with 50% acetic acid at 19.2 ml/hr, collecting 6.4 ml fractions. Fractions 27–39 were pooled, evaporated and the residue dried over KOH under high vacuum (67.5 mg). This residue was applied to a CM-52 ion-exchange column (30×1 cm) and eluted with an ammonium acetate gradient 0.05M to 0.5M over 2 days at 5.8 ml/hr collecting 2.9 ml fractions. After collecting 50 fractions, no peak assignable to the product was obtained on the trace. Therefore, the column was eluted with 0.5M ammonium acetate taking 5.8 ml fractions. The product from fraction 55 was found to be pure. Lyophilisation afforded 7.4 mgs of pure material.

H-176    $C_{60}H_{82}O_{10}N_{14}$    MW: 1099.356
TLC:    Rf = 0.4 in EtoAc/Py/AcoH/H₂O    (20:20:6:11)
on silica plates
Amino acid analysis: after hydrolysis in 6N HCl
plus phenol for 92 hrs, 110°, peptide content 88.6%
His: 2.97; Pro: 1.1, Val: 0.98; Ile: 0.97; Phe: 0.99

EXAMPLE 2

H-189,
H—Pro—His—Pro—Phe—His—S-
ta—Val—Ile—His—Lys—OH       (XXXVI)

Solid-phase synthesis of this peptide was carried out by the described procedure starting with 1.2 grams (0.24 mmole) of Boc-Lys(Cl₂Z)—O—Resin. In the subsequent coupling reactions, 1 mmole of Boc—amino acid was used except for Boc—Statine of which 0.36 mmoles were used. The dried peptide-Resin ester weighed 1.53 grams.

0.6 grams of this material were subjected to HF+ anisole treatment and afforded a residue of 171.6 mgs. This residue was applied to a G-25 Sephadex column (82×2.5 cm) eluted with 50% acetic acid at 19.2 ml/hr collecting 6.4 ml fractions. Fractions 32–42 provided 121.6 mgs of residue. Half of this material was applied to a CM-52 ion-exchange column (30×1 cm), eluted with an ammonium acetate buffer gradient from 0.05M to 1M over 2 days at 5.8 ml/hr collecting 2.9 ml fractions. Fraction 33 afforded pure product which upon lyophilisation gave 9.5 mgs of material.

H-189    $C_{66}H_{101}O_{12}N_{17}$    MW: 1204.535
TLC (silica)    Rf = 0.5 in EtoAc/Py/AcoH/H₂O    (15:20:6:11)
Amino acid analysis after hydrolysis with 6N HCl + phenol at 110°/40 hrs:

His: 3.03; Ile: 0.90; Phe: 0.86; Pro: 2.19; Val: 0.94
Peptide content 80.1%.

Use of the compounds

Either of the above compounds may be given, as described earlier herein, in amounts of for example 0.1 mg/kg body weight daily in diagnosis of high-renin states and in therapy of heart failure and hypertension.

We claim:

1. Polypeptides of the general formula:

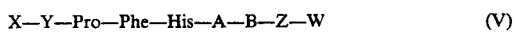

X—Y—Pro—Phe—His—A—B—Z—W    (V)

or the partial sequences

X—A—B—Z—W    (V) (i)

X—His—A—B—Z—W    (V) (ii)

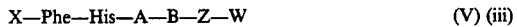

X—Phe—His—A—B—Z—W    (V) (iii)

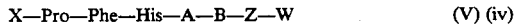

X—Pro—Phe—His—A—B—Z—W    (V) (iv)

where
Pro, Phe or His are unsubstituted or substituted with OH, F, Cl, Br or Me;
X=hydrogen, an amino-nitrogen protecting group selected from lower alkyl, acetyl, pivaloyl, t-butoxy-carbonyl, benzyloxycarbonyl or benzoyl and said lower alkyl group is a $C_1$-$C_5$ alkyl group or an amino acyl selected from D- and L-Pro, Val or Ile, or Gly;
Y=a D- or L-His;

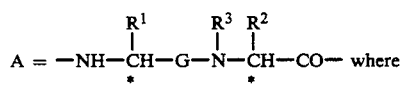

$$A = -NH-\overset{R^1}{\underset{*}{CH}}-G-\overset{R^3}{N}-\overset{R^2}{\underset{*}{CH}}-CO- \text{ where}$$    (VI)

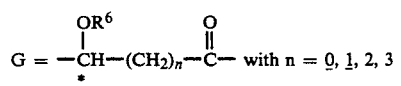

$$G = -\overset{OR^6}{\underset{*}{CH}}-(CH_2)_n-\overset{O}{\overset{\|}{C}}- \text{ with } n = \underline{0}, \underline{1}, 2, 3$$    (VII)

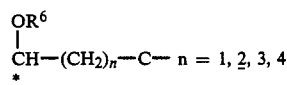

$$\overset{OR^6}{\underset{*}{CH}}-(CH_2)_n-C- \quad n = 1, \underline{2}, 3, 4$$    (VIII)

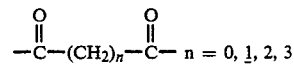

$$-\overset{O}{\overset{\|}{C}}-(CH_2)_n-\overset{O}{\overset{\|}{C}}- \quad n = 0, \underline{1}, 2, 3$$    (IX)

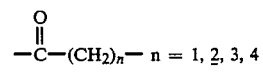

$$-\overset{O}{\overset{\|}{C}}-(CH_2)_n- \quad n = 1, \underline{2}, 3, 4$$    (X)

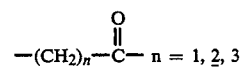

$$-(CH_2)_n-\overset{O}{\overset{\|}{C}}- \quad n = 1, \underline{2}, 3$$    (XI)

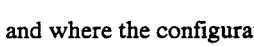

and where the configuration at asymmetric centres * is either R or S and $R^1$ and $R^2$ are isopropyl, isobutyl or benzyl;
$R^3$=hydrogen or an amino-nitrogen protecting group;
$R^6$=hydrogen or a hydroxyl protecting group;
B=a lipophilic amino acyl residue
Z=D- or L-His residue; and
W=a hydroxyl group, an amide nitrogen group, or a basic amino acyl residue selected from D- or L-serine, D- or L-lysine, D- or L-arginine or amino alcohol residue derived therefrom; or
Z+W=the amino alcohol residue corresponding to the amino acyl residue Z.

2. A polypeptide according to claim 1, wherein of said Pro Phe and His are substituted in the ring, Pro by OH, Phe by OH, F, Cl, Br or Me, His by Me.

3. A polypeptide according to claim 1, wherein of said Pro, Phe and His are replaced by, respectively, 4-hydroxyproline or pGlu; Tyr, Phe(4—Cl) or Phe(-4—F); His (Me) or spinacin.

4. A polypeptide according to claim 1 wherein said protecting group X is an acyl or lower alkyl group.

5. A polypeptide according to claim 4 wherein said acyl group is acetyl, pivaloyl, t-butoxycarbonyl benzyloxycarbonyl or benzoyl and said lower alkyl group is a $C_1$-$C_4$ alkyl group.

6. A polypeptide according to claim 1, wherein said amino acyl group X is D- or L-Pro, Val or Ile, or Gly.

7. A polypeptide according to claim 1, wherein said amino acyl residue Y is D- or L-His.

8. A polypeptide according to claim 1, wherein said amino acid side chains $R^1$ and $R^2$ are lipophilic or aromatic, Leu, Ile, Val, Phe cyclohexyl—Ala, adamantyl—Ala, or Phe Tyr Trp or His.

9. A polypeptide according to claim 8, wherein said side chains are selected from isopropyl, isobutyl and benzyl.

10. A polypeptide according to claim 1, wherein said protecting group $R^3$ is lower alkyl, lower acyl, —$SO_2Ph$, —$SO_2C_6H_4CH_3(p)$, t-butoxy carbonyl, a benzyloxycarbonyl.

11. A polypeptide according to claim 10, wherein said alkyl or acyl group is a $C_1$-$C_5$ group.

12. A polypeptide according to claim 1, wherein said hydroxyl protecting group $R^6$ is lower alkyl, lower acyl, benzyl or tetrahydropyranyl.

13. A polypeptide according to claim 12, wherein said alkyl or acyl group is a $C_1$-$C_5$ alkyl or acyl group.

14. A polypeptide according to claim 1, wherein said residue B is a D- or L-Val, Leu or Ile residue.

15. A polypeptide according to claim 1, wherein said residue Z is a D- or L-Tyr, Phe or His residue.

16. A polypeptide according to claim 1, wherein said hydroxyl group W is protected in ester form.

17. A polypeptide according to claim 16, wherein said protecting group is lower alkanoyl or cycloalkanoyl or benzoyl.

18. A polypeptide according to claim 17, wherein said lower alkanoyl group is a $C_1$-$C_5$ alkanoyl group and said cycloalkanoyl group a $C_3$-$C_7$ cycloalkanoyl group.

19. A polypeptide according to claim 1, wherein said amide nitrogen group W is in protected form.

20. A polypeptide according to claim 19, wherein said amide nitrogen protecting group is —$NHR^5$ or —$N(R^5)_2$ where $R^5$ is lower alkyl and $(R^5)_2$ is two lower alkyl groups the same or different or a cycloalkyl group.

21. A polypeptide according to claim 20, wherein said alkyl group is a $C_1$-$C_5$ alkyl group and said cycloalkyl group is a $C_3$-$C_7$ cycloalkyl group.

22. A polypeptide according to claim 19, wherein said amide nitrogen protecting group is —NH—($CH_2$)$_n$—Q or $NR^5$—($CH_2$)$_n$—Q where n=2 to 6 and Q=an amino or guanidyl group where $R^5$ is lower alkyl.

23. A polypeptide according to claim 22, wherein one or more of the hydrogens attached to nitrogen in said protecting group is replaced by $R^5$ or $(R^5)_2$, defined as in claim 20.

24. Polypeptides according to claim 23, wherein $R^5$ is $C_1$-$C_5$ alkyl group and $(R^5)_2$ is $C_1$-$C_5$ alkyl group or a $C_3$-$C_7$ cycloalkyl.

25. A polypeptide according to claim 1, wherein said amino acid residue W is a D- or L-Ser, Lys or Arg residue.

26. A polypeptide according to claim 25, wherein said residue is in the form of the corresponding amide.

27. A polypeptide according to claim 26, wherein said amide is in protected form.

28. Polypeptides according to claim 27, wherein said amide nitrogen protecting group is —NHR$^5$ or —N(R$^5$)$_2$ where R$^5$ is lower alkyl and (R$^5$)$_2$ is two lower alky groups the same or different or a cycloalkyl group.

29. Polypeptides according to claim 28, wherein the alkyl group is a $C_1$-$C_5$ alkyl group and the cycloalkyl group is a $C_3$-$C_7$ cycloalkyl group.

30. A polypeptide according to claim 25, wherein said residue is protected in ester form.

31. Polypeptides according to claim 30, wherein said esterifying group is lower alkanoyl, cycloalkanoyl or benzoyl.

32. A $C_1$-$C_5$ alkyl group or a $C_3$-$C_7$ cycloalkyl group.

33. A polypeptide according to claim 1, wherein said amino alcohol residue W is the amino alcohol residue derived from D- or L-Ser, Lys or Arg.

34. A polypeptide according to claim 1, wherein said amino alcohol residue Z+W is derived from D- or L-Tyr, Phe or His.

35. A polypeptide according to claim 33 wherein said amino alcohol residue is in protected ester or ether form.

36. Polypeptides according to claim 33 wherein said amino alcohol residue is in protected form the protective group is selected from lower alkyl, lower acyl, benzyl and tetrahydropyranyl.

37. A polypeptide according to claim 33 wherein said amino alcohol residue is in protected form the protective group being as set out for $R^6$ in claim 13.

38. A polypeptide according to claim 1, wherein G is selected from:

1  $\underset{*}{-\text{CH}}-\text{CH}_2-\text{CO}-$ with OH on CH  (XXVI)

2  $\underset{*}{-\text{CH}}-\text{CH}_2-\text{CH}_2-$ with OH on CH  (XXVII)

3  $-\overset{\text{O}}{\underset{\|}{\text{C}}}-\text{CH}_2-\text{CO}-$  (XXVIII)

4  $-\text{CH}_2-\text{CH}_2-\text{CO}-$  (XXIX)

5  $\underset{*}{-\text{CH}}-\text{CO}-$ with OH on CH  (XXX)

6  $\underset{*}{-\text{CH}}-\text{CH}_2-$ with OH on CH  (XXXI)

7  $-\overset{\text{O}}{\underset{\|}{\text{C}}}-\text{CO}-$  (XXXII)

8  $-\text{CH}_2-\text{CO}-$  (XXXIII)

9  $-\overset{\text{O}}{\underset{\|}{\text{C}}}-\text{CH}_2-$  (XXXIV)

39. A polypeptide according to claim 1, wherein said polypeptide analogue is in further modified form by isosteric replacement of remaining peptide bonds by $$-\text{NH}-\underset{*}{\overset{R^1}{\text{CH}}}-\text{CH}_2-\underset{R^3}{\overset{R^2}{\text{N}}}-\underset{*}{\overset{}{\text{CH}}}-\text{C}\overset{\displaystyle\diagup\!\!\!\!\text{O}}{\diagdown}$$  (XIII)

"reduced" isostere bond or $$-\text{NH}-\underset{*}{\overset{R^1}{\text{CH}}}-\text{C}\underset{\diagdown\text{CH}_2-\underset{*}{\overset{R^2}{\text{CH}}}-\text{C}\overset{\diagup\!\!\!\text{O}}{\diagdown}}{\overset{\diagup\!\!\!\text{O}}{}}$$  (XIV)

"keto" isostere bond or $$-\text{NH}-\underset{*}{\overset{R^1}{\text{CH}}}-\text{CH(OH)}-\text{CH}_2-\underset{*}{\overset{R^2}{\text{CH}}}-\text{C}\overset{\diagup\!\!\!\text{O}}{\diagdown}$$  (XV)

"hydroxy" isostere bond or $$-\text{NH}-\underset{*}{\overset{R^1}{\text{CH}}}-\text{CH}_2-\text{CH}_2-\underset{*}{\overset{R^2}{\text{CH}}}-\text{C}\overset{\diagup\!\!\!\text{O}}{\diagdown}$$  (XVI)

"hydrocarbon" isostere bond where the significance of *, $R^1$, $R^2$ and $R^3$ is as before.

40. A polypeptide according to claim 39, wherein one or both of the Pro-Phe and Phe-His bonds in formula V is the site of the isosteric replacement.

41. A polypeptide according to claim 1, wherein said polypeptide analogue is in protected form at amino, amide, carboxyl, hydroxy or other reactive groups, or in salt form at amino, imidazole or carboxyl groups.

42. A polypeptide according to claim 41, wherein said salt is an acid addition salt at one or more basic centres.

43. The polypeptide:

H-His-Pro-Phe-His-Sta-Val-Ile-His-OH or

H-Pro-His-Pro-Phe-His-Sta-Val-Ile-His-Lys-OH.

44. Polypeptides as in claim 43 but having the —CH(OH)CH$_2$CO— link of the statine residue replaced by a link selected from:

| 1 | $\underset{*}{-\overset{OH}{\underset{|}{CH}}-CH_2-CO-}$ | (XXVI) |
|---|---|---|
| 2 | $\underset{*}{-\overset{OH}{\underset{|}{CH}}-CH_2-CH_2-}$ | (XXVII) |
| 3 | $-\overset{O}{\underset{\|}{C}}-CH_2-CO-$ | (XXVIII) |
| 4 | $-CH_2-CH_2-CO-$ | (XXIX) |
| 5 | $\underset{*}{-\overset{OH}{\underset{|}{CH}}-CO-}$ | (XXX) |
| 6 | $\underset{*}{-\overset{OH}{\underset{|}{CH}}-CH_2-}$ | (XXXI) |
| 7 | $-\overset{O}{\underset{\|}{C}}-CO-$ | (XXXII) |
| 8 | $-CH_2-CO-$ | (XXXIII) |
| 9 | $-\overset{O}{\underset{\|}{C}}-CH_2-$ | (XXXIV) |

45. A diagnostic test for high renin states wherein a polypeptide analogue according to claim 1, is administered, a positive result being indicated by a fall in blood pressure related to said administration.

46. A treatment of heat failure wherein an effective amount of a polypeptide according to claim 1, is administered.

47. A treatment of hypertension wherein an effective amount of a polypeptide according to claim 1, is administered.

48. Test or treatment according to claim 45, wherein 0.001 to 10 mg/kg body weight of the analogue is administered daily.

49. A pharmaceutical composition comprising a renin-inhibiting amount of polypeptide analogue according to claim 1, in a pharmaceutically acceptable medium.

50. Polypeptide analogue of the general formula:

$$X-Y-Pro-Phe-His-A-B-Z-W \quad (V)$$
$$\phantom{X-Y-Pro-Phe-}6\ \ 7\ \ \ 8\ \ \ \ 9\ \ 10,11\ 12\ 13$$

or the partial sequences:

| X-A-B-Z-W | (V) (i) |
| X-His-A-B-Z-W | (V)(ii) |
| X-Phe-His-A-B-Z-W | (V) (iii) |
| X-Pro-Phe-His-A-B-Z-W | (V) (iv) | where:
Pro, Phe, and His is unsubstituted or substituted with OH, F, Cl, Br or Me;

X=H; or an acyl or other N-protecting group selected from acetyl, pivaloyl, benzyloxycarbonyl, t-butyloxycarbonyl, benzoyl or lower alkyl or an D- or L-amino acyl residue Y=D- or L-His or other D- or L-basic or aromatic amino-acyl residue, or is absent;

$$A = -NH-\overset{R^1}{\underset{|}{\underset{*}{CH}}}-G-\overset{R^3}{\underset{|}{N}}-\overset{R^2}{\underset{|}{\underset{*}{CH}}}-CO- \text{ where} \quad (VI)$$

$$G = -\underset{*}{\overset{OR^6}{\underset{|}{CH}}}-(CH_2)_n-\overset{O}{\underset{\|}{C}}- \text{ with } n = 0, 1, 2, 3 \quad (VII)$$

$$-\underset{*}{\overset{OR^6}{\underset{|}{CH}}}-(CH_2)_n- \quad n = 1, 2, 3, 4 \quad (VIII)$$

$$-\overset{O}{\underset{\|}{C}}-(CH_2)_n-\overset{O}{\underset{\|}{C}} \quad n = 0, 1, 2, 3 \quad (IX)$$

$$-\overset{O}{\underset{\|}{C}}-(CH_2)_n- \quad n = 1, 2, 3, 4 \quad (X)$$

$$-(CH_2)_n-\overset{O}{\underset{\|}{C}}- \quad n = 1, 2, 3 \quad (XI)$$

and where the configuration at asymmetric centres * is either R or S, $R^1$ and $R^2$, the same or different, being $=^iPr$ (isopropyl), $^iBu$ (isobutyl), Bzl (benzyl) or other amino-acid side chain preferably lipophilic or aromatic;

$R^3$=H; lower alkyl ($C_1$-$C_5$); or t-butyloxycarbonyl, benzyloxycarbonyl, ring substituted benzyloxycarbonyl, $-SO_2PH$, $-SO_2C_6H_4CH_3(p)$, formyl or other N-protecting group including lower acyl ($C_1$-$C_5$) generally;

$R^6$=H, or lower alkyl, lower acyl, benzyl, tetrahydropyranyl, or other hydroxyl protecting group;

B=D- or L-Val Leu or Ile or other D- or L-lipophilic amino-acyl residue;

Z=D- or L-Tyr, Phe, His or other L- or D-aromatic amino-acyl residue; and

W=(i)-OH as such or in protected ester form e.g. as $-OR^4$ where $R^4$=lower alkyl primarily $C_1$-$C_5$ and particularly $^tBu$, or cycloalkyl primarily $C_3$-$C_7$, or Bzl, or other ester forming group; or (ii) $-NH_2$, as such, or in protected amide form as $-NHR^5$ or $-N(R^5)_2$ (where $R^5$=an N-protecting or other substituent group e.g. lower alkyl as for $R^4$ and $(R^5)_2$=two such groups or e.g. cyclo-alkyl, primarily $C_3$-$C_7$), or as $-NH-(CH_2)_n-Q$ or $-NR^5-(CH_2)_n-Q$ (where n=2 to 6 and Q=$NH_2$ or $$-NH-C\underset{NH_2}{\overset{\displaystyle\nearrow NH}{\diagdown}}$$

and wherein any of the hydrogens attached to nitrogen may be substituted by $R^5$ or $(R^5)_2$); or (iii) an D- or L-serine or D- or L-lysine, arginine or other basic amino-acyl residue as such or in amide form, substituted amide form or ester form e.g. containing a group or groups as given for $R^4$ and $R^5$ above as the case may be; or (iv) an amino alcohol residue derived therefrom as such or protected in ester or ether form e.g. containing a group as given for $R^4$ above or Z+W=an alcohol derived from L- or D-Tyr, Phe or His or other L- or D-aromatic amino-acyl residue as such or protected in ester or ether form as above; such polypeptide being in the above form or modified by isosteric replacement of one or more remaining peptide bonds, for example by reduced —CH$_2$—NH—, keto,

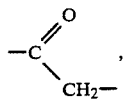

hydroxy, —CH(OH)—CH$_2$—, or hydrocarbon —CH$_2$—CH$_2$— isosteric links in the form:

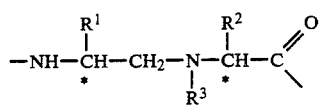 (XIII)

"reduced" isostere bond or

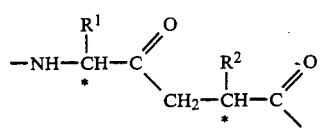 (XIV)

"keto" isostere bond or

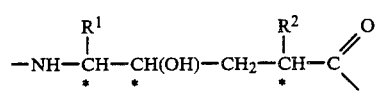 (XV)

"hydroxy" isostere bond or

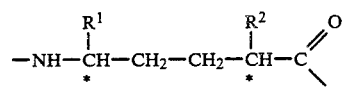 (XVI)

"hydrocarbon" isostere bond where the significance of *, $R^1$, $R^2$ and $R^3$ is as before; and said polypeptide further being in free form or in protected form at one or more remaining amino or amide (including peptide) nitrogen, carboxyl, hydroxy or other reactive groups, or in salt form at amino, imidazole or carboxyl groups, in particular as their physiologically acceptable acid addition salts at basic centres.

51. Polypeptides according to claim 1 wherein G is

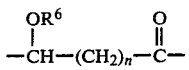

and n=0 or 1.

52. Polypeptides according to claim 1 wherein G is

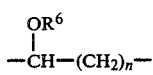

and n=2.

53. Polypeptides according to claim 1 wherein G is

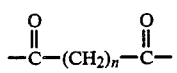

and n=1.

54. Polypeptides according to claim 1 wherein G is

and n=2.

55. Polypeptides according to claim 1 wherein G is

and n=2.

* * * * *